United States Patent [19]

Willis et al.

[11] Patent Number: 4,718,423
[45] Date of Patent: Jan. 12, 1988

[54] MULTIPLE-FUNCTION CARDIOVASCULAR CATHETER SYSTEM WITH VERY HIGH LUMENAL EFFICIENCY AND NO CROSSOVERS

[75] Inventors: Allan F. Willis, Newbury Park; Byron L. Moran, Santa Barbara, both of Calif.

[73] Assignee: Spectramed, Inc., Newport Beach, Calif.

[21] Appl. No.: 920,736

[22] Filed: Oct. 17, 1986

[51] Int. Cl.⁴ .............................................. A61B 5/02
[52] U.S. Cl. .................... 128/634; 128/693; 128/713; 128/736; 128/673; 128/419 P; 128/786
[58] Field of Search ............... 128/691–693, 128/713, 665–667, 632, 635, 736, 734, 419 P, 786

[56] References Cited

U.S. PATENT DOCUMENTS

| | | | |
|---|---|---|---|
| 3,995,623 | 12/1976 | Blake et al. | 128/642 |
| 4,201,222 | 5/1980 | Haase | 128/667 X |
| 4,328,806 | 5/1982 | Cooper | 128/642 X |
| 4,329,993 | 5/1982 | Lieber et al. | 128/691 X |
| 4,380,237 | 4/1983 | Newbower | 128/734 X |
| 4,476,877 | 10/1984 | Barker | 128/692 X |
| 4,502,488 | 3/1985 | Degironimo et al. | 128/692 |

*Primary Examiner*—William E. Ramm
*Assistant Examiner*—Angela D. Sykes
*Attorney, Agent, or Firm*—Romney Golant Martin Seldon & Ashen

[57] ABSTRACT

Cardiac output, blood oxygen saturation, and oxygen consumption are measured using only two lumens of a catheter that has no interlumen crossover. Therefore this construction avoids costly techniques for modifying the catheter, as well as leakage risk at crossover points. Cardiac output is measured by thermodilution, and venous blood oxygen by optical scattering measurements through optic fibers; oxygen consumption is then claculable from the cardiac output and venous oxygen saturation—and independently measured arterial saturation. Cold-bolus injection uses on lumen. The thermal-sensor leads (electrical or otherwise) and optic fibers share the other lumen, through which they are drawn together: this method of installation effects yet a further economy by saving an expensive labor step, and tends to prevent the leads and fibers from damaging one another. Addition of a balloon and a separate inflation lumen permits balloon functions as well, now using only three lumens and still without lumenal crossovers—and without risk of balloon deflation due to air leaks associated with the thermal sensors. Adding yet another one or two separate lumens permits provision of a pacing wire or pulmonary-artery pressure measurement, or both, with a respective total of only four or five lumens.

13 Claims, 4 Drawing Figures

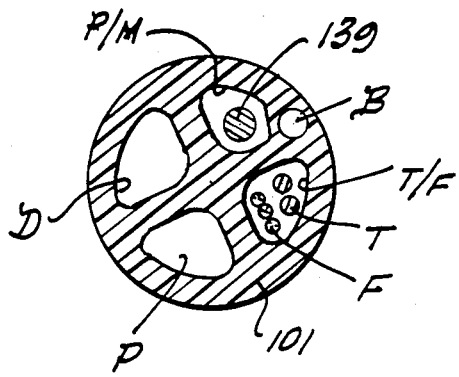
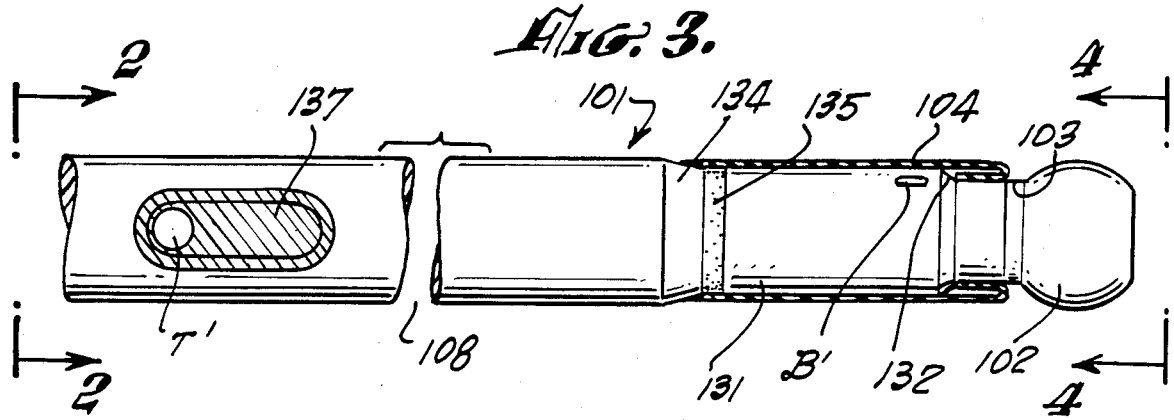
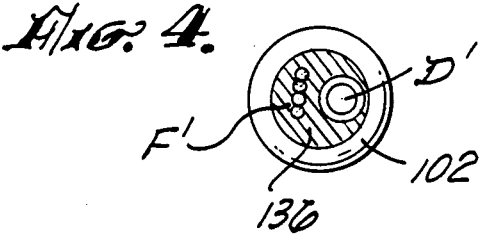

MULTIPLE-FUNCTION CARDIOVASCULAR CATHETER SYSTEM WITH VERY HIGH LUMENAL EFFICIENCY AND NO CROSSOVERS

BACKGROUND

1. Field of the Invention

This invention relates generally to cardiovascular diagnostic and therapeutic catheter systems, and more particularly to such systems that perform three or more functions—including measurement of cardiac output, blood oxygen saturation, and oxygen consumption.

2. Prior Art

One major thrust in the recent prior art of cardiovascular catheter systems is represented by a group of U.S. patents assigned variously by Lieber, Cooper and Estes to American Hospital Supply Corporation—particularly including U.S. Pat. Nos. 4,328,806, 4,329,994, 4,329,993 and 4,407,304.

These patents introduce and explain the great medical importance of multiple-function cardiac catheters (with pacemakers, balloons, etc.) and the extreme desirability of reducing the outside diameter of such a catheter—and, consequently, the number of lumens in such a catheter.

These patents also chronicle the major difficulty which workers in this field encountered before 1980 in trying to effect such reductions: "[I]n order to achieve multiple functions in a cardiac catheter of optimum size, it has generally been considered necessary to compromise the performance capabilities of such a catheter."

The patentees sought to avoid such compromises by carrying electrical conductors or even a gas pathway (for balloon inflation or pressure monitoring) across the boundary septum between two lumens within a catheter. They allocate different functions to different segments of one lumen (and sometimes of two lumens) within the catheter. Thereby, in effect, they make double use of a single lumen.

It is not our intention to criticize unduly the innovations described in these patents, which are considered significant and valuable. In our view, however, the approach adopted by Lieber et al. to minimizing the number of lumens in a cardiovascular catheter is itself characterized by undesirable compromises.

First, that approach involves quite elaborate, expensive techniques for forming an aperture in the septum between lumens, and for installing (or forming in situ) one or more plugs or like structures in the same region. Some of these structures must contain pressure sensors or like devices. The lumens and septa in question are quite tiny, and these mechanical modifications are necessarily fussy, time consuming and, at least as we see it, susceptible to error—with potentially disastrous results.

Second, the Lieber et al. approach inherently leaves a substantial disruption in the catheter structure. Whether the catheter is locally weakened or strengthened is beside our point, which is that the catheter symmetry and the rough isotropy of its materials are substantially disrupted, leading inevitably to problems in operation within the human cardiovascular system.

Such a catheter perhaps may not actually fail in a gross mechanical sense—e.g., tearing away adjacent to the plug. It seems to us very likely, however, that some unacceptable incidence of balloon deflation will occur due to small air leaks around the pressure sensors or other devices that are mounted in the plugs. In short the solution offered by these patents appears to us unacceptable on grounds of questionable inherent reliability as well as high cost.

It is very desirable to achieve high efficiency in the use of a limited number of lumens, so that several diagnostic and therapeutic functions can be performed using a catheter of very small diameter. Yet it is also essential to achieve this goal without introducing additional points of weakness, either mechanical or economic.

Another group of prior patents that may be related to the present invention is granted variously to Shaw, Sperinde, Goldring and Miller, assignors to Oximetrix, Inc. These patents disclose catheter instrumentation and related methods for measuring oxygen saturation in blood.

The instruments monitor optical scattering at two or three different wavelengths, through optic fibers emplaced in the catheters. It is known that such measurements in effect complement the slightly older catheter-effected measurements of cardiac output (by thermodilution) and of pressure at several points in the heart and adjacent blood vessels, as well as balloon functions and pacing.

In particular, the oxygen saturation in the pulmonary artery presents an ideal average value of venous oxygen saturation. This value may be subtracted from an independently measured value of arterial oxygen saturation—which is obtainable straightforwardly by other, conventional techniques—to find the "arterial-venous difference" or change in blood oxygen saturation "across" the body considered as an oxygen-consumption system.

This arterial-venous difference multiplied by the cardiac output (and corrected for hemoglobin concentration and a dimensional constant) then yields the rate of oxygen consumption by the body.

Prior catheter systems for measuring both oxygen saturation and cardiac output (and thus oxygen consumption) have suffered from either the undesirably large diameter of the catheters employed—as explained in the Lieber patents—or from the high costs and unique potential failure modes of the Lieber et al. lumenal-crossover catheters.

Apart from crossover catheters, it has been regarded among persons skilled in the art of cardiovascular catheter technology as essentially impossible to provide a full complement of cardiovascular diagnostic and therapeutic functions in a catheter of 7 or 7.5 French. (The "French" is a customary unit of measure for catheter and needle diameters, one French being equal to a third of a millimeter.) Yet that catheter size is considered the largest permissible for most adult patients.

In view of these limitations as distinct teachings of the prior art, modern proposals to build small but extremely reliable multipurpose commercial catheters have been regarded by persons skilled in the art as essentially unfeasible.

(By "multipurpose" catheters we here mean catheters capable of not only oxygen-consumption measurements but also balloon functions, pacing, and pulmonary-artery pressure monitoring, and in some cases carrying a strength member of Kevlar ® fiber or the like.)

It nevertheless remains extremely desirable, for several reasons, to provide just such catheters. The alternative, very unsatisfactory, is to perform repetitive catheterizations with different catheters, attempting to obtain a full set of data. Cardiovascular diagnostic data, however, should be time-correlated, and they cannot be with serial measurements using different catheters.

Considerable diagnostic difficulty results. This diagnostic difficulty is compounded, to put it mildly, by the inability of many heart patients to stand up to a regimen of testing that is thus protracted.

A final reason, which is really reason enough itself, is in human terms: the extreme aggravation and discomfort undergone by the typically feeble and unwell heart patients being tested and treated. For them this type of testing and therapy is a vital necessity, but at the same time can be a thoroughly miserable experience.

SUMMARY OF THE DISCLOSURE

Our invention is a cardiovascular diagnostic and therapeutic catheter system for determining cardiac output, blood oxygen saturation, and oxygen consumption in a human patient. The system incorporates a catheter of advantageously limited diameter without any interlumen crossovers.

The system includes a catheter that has at least two lumens. The catheter has a distal end adapted for insertion through the patient's vascular system and heart. The catheter also has a proximal end that is adapted for functional attachment to apparatus outside the patient's body.

(In the field of invasive medical instrumentation there is a serious inconsistency in use of the terms "distal" and "proximal." Physicians and other medical personnel sometimes refer these terms to the patient's body. Instrument development personnel usually reverse the frame of reference, referring the same terms to the electronics module outside the patient's body, at the other end of the instrumentation system. The latter convention is used here—as is clear in the preceding paragraph.)

In the side of the catheter, at a first measured distance from the distal end, is an orifice communicating with a first one of the two lumens. This orifice is adapted for passage of liquid from that first lumen into the patient's vascular system.

The system also includes some means for forcing passage of liquid from that first lumen through the orifice into the patient's vascular system. For purposes of speaking generally, we will call these means the "injecting means." The injecting means are outside the patient's body and communicating with a proximal portion of the first lumen.

Also included within the system is at least one temperature-measuring device. This device is disposed along the catheter, near the distal end of the catheter, for exposure to temperatures of the patient's vascular system.

In addition the system includes some means for carrying information or "signals" from the temperature-measuring device. These means will be called, also for purposes of generality in expression, the "signal-carrying means."

They are long, thin, and disposed within only the second one of the two lumens—that is, free of interlumen crossover into the first lumen. The signal-carrying means and the temperature-measuring device are functionally interconnected.

It is also part of our invention to provide some means for utilizing the temperature-measuring device to measure the temperature within the patient's vascular system. We will call these means the "signal-utilization means." They are outside the patient's body and interconnected with the signal-carrying means at a proximal portion of the second lumens.

By virtue of only those features of our invention that have been described so far in this document, the temperature-measuring device and the signal-utilization means in combination are responsive to temperature variations resulting from forced passage of liquid through the first lumen.

Our invention, however, also necessarily includes certain other features: among these must be some means for measurement of oxygen saturation of the patient's blood. These means operate by projection of light (which may be infrared or ultraviolet light, as well as visible light) through one or more optic fibers; in this document we therefore call them "optical-fiber means."

These optical-fiber means are also disposed within the second lumen. They are adapted to project light from the distal end of the catheter into the patient's vascular system and to receive light reflected back from the patient's vascular system.

Our invention must further include some means for transmitting light through the optical-fiber means to be projected into the patient's vascular system. We will call these means the "light-emitting means." They are disposed outside the patient's body and interconnected with the optical-fiber means at a proximal portion of the catheter.

Yet further necessarily included within our invention are some means for receiving light through the optical-fiber means after reflection back from the patient's vascular system. We will call these the "light-detecting means." They are disposed outside the patient's body and interconnected with the optical-fiber means at a proximal portion of the catheter. They are also adapted for interpretation of the received light to determine oxygen saturation of the patient's blood.

Now by operation of the catheter system described above, our invention provides measurements of cardiac output and oxygen saturation, and, by calculation therefrom, measurement of oxygen consumption in the patient—using only the two lumens mentioned, and without any interlumen crossover of signal-carrying means (or of gas passageways).

While the foregoing may describe our invention in its broadest or most general form, we prefer to obtain enhanced benefits by adding other features. Some of these preferred additional features will now be described.

First, we consider it advantageous to provide an additional lumen in the catheter, and an inflatable balloon near the distal end of the catheter and communicating with a distal portion of the additional lumen. Cooperating with the balloon and the additional lumen are balloon-inflating means outside the patient's body. These external balloon-inflating means communicate with a proximal portion of the additional lumen. Thus the additional lumen serves for inflation (and deflation) of the balloon.

The signal-carrying means mentioned earlier are entirely outside the "additional" balloon lumen. This preferred form of our catheter system not only provides the measurements already enumerated but also provides balloon functions, using only three lumens—and, again, without any interlumen crossover of the signal-carrying means. In this form or embodiment of our invention, since the balloon uses its own dedicated lumen, operation of the catheter system is free from risk of balloon deflation due to air leaks associated with the temperature-measuring means.

Secondly, there is another preferred embodiment of our invention for use with a voltage supply outside the patient's body. This embodiment includes yet another lumen defined within the catheter, and there is also a second orifice in the side of the catheter—at a second measured distance from the distal end of the catheter. This second orifice communicates with the "yet another" lumen just noted.

In this second preferred embodiment now under discussion, a coaxial electrical wire is disposed within the "yet another" lumen. The wire has a proximal end adapted for functional attachment to the outside voltage supply, and a distal end that projects through the second orifice into the patient's vascular system.

Thirdly, we also prefer to provide our invention in a form that is intended for use with pressure-measuring means disposed outside the patient's body. This form further includes still another lumen within the catheter. There is an orifice in the catheter substantially at the distal end, communicating with this "still another" lumen.

In this third preferred form of our invention there are also means, outside the patient's body, for establishing a column of liquid within the "still another" lumen; and means for functionally interconnecting the pressure-measuring means to the "still another" lumen to monitor pressure in the liquid column inside that lumen.

By virtue of the combined features of this third preferred embodiment, the catheter system provides the earlier-enumerated measurements, and in addition the pressure-measuring means monitor pressure within the patient's vascular system, substantially at the distal end of the catheter.

We mean it to be understood that any of these three preferred forms just discussed may be employed alone—that is to say, any of the three add-on features may be combined with only the more basic two-lumen catheter first described—or may be employed in any combination of two or three preferred embodiments as desired, to provide a catheter of three, four or five lumens that performs the corresponding combinations of functions.

Other aspects of our invention that we consider desireable and preferable but that may not be strictly necessary will be taken up in the detailed discussion that follows. All of the foregoing operational principles and advantages of the present invention will be more fully appreciated upon consideration of the following detailed description, with reference to the appended drawings, of which:

BRIEF DESCRIPTION OF THE DRAWINGS

FIG. 2 is a cross-section of the same embodiment, taken along the line 2—2 in FIG. 1 (and in FIG. 3).

FIG. 3 is a cross-sectional elevation or plan of the same embodiment, partially in section, near the distal end of the catheter.

FIG. 4 is an end elevation of the same embodiment, taken along the line 4—4 in FIGS. 1 and 3 at the distal end of the catheter.

DETAILED DESCRIPTION OF THE PREFERRED EMBODIMENTS

Figure 1:
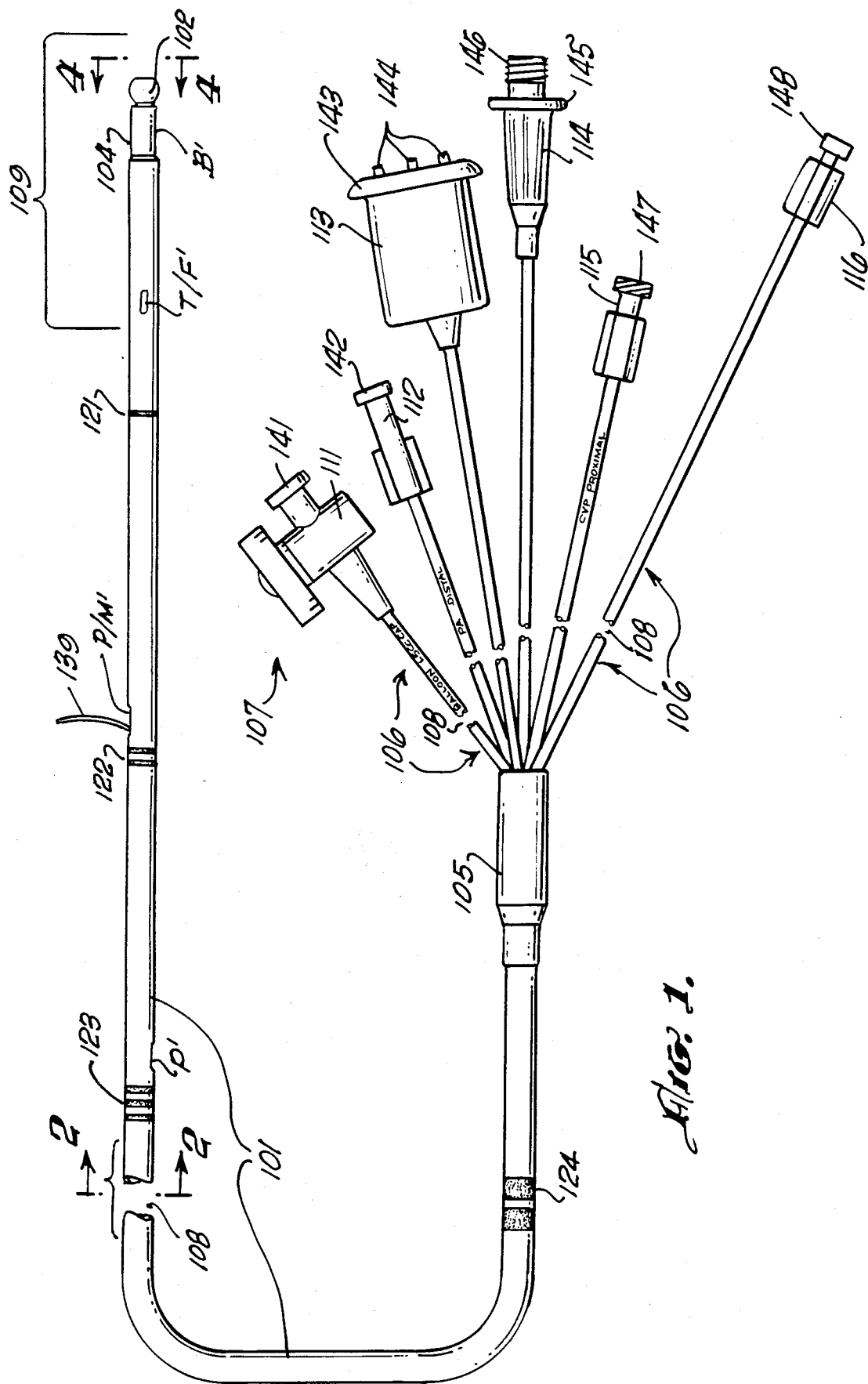
FIG. 1 is a somewhat schematic view, which may be considered either a plan or an elevation, of a catheter system in accordance with a preferred embodiment of our invention. Because of the considerable length of the instrument, it is drawn partially broken away.

As shown in FIGS. 1 and 2, the preferred embodiment of our invention makes use of a five-lumen catheter 101. The catheter diameter is preferably 7.5 French or less.

Fixed at the proximal end of the catheter 101 are a manifold connector 105 and five individual single-lumen tubes 106. These individual tubes respectively communicate at their distal ends with the five lumens T/F, P, B, D and P/M of the catheter 101—through the manifold connector 105—and at their proximal ends with five termination devices 107.

Likewise fixed at the distal end of the catheter 101 are a molded tip 102 and an annular balloon 104. In the tip 102 is the polished distal end F' (FIG. 4) of a bundle of optical fibers F (FIG. 2), that is drawn through the lumen T/F in the catheter 101. Also in the tip 102 is a port or aperture D' (FIG. 4).

This distal aperture D' effectively constitutes the distal end of one of the lumens D (FIG. 2) in the catheter 101. The remaining space in the orifice of the tip is occupied with epoxy or like inert potting material 136.

As is well known in the cardiovascular field, a catheter of this general sort is inserted through the patient's vena cava into the right atrium and ventricle, with the tip 103 and its distal aperture D' extending onward into the patient's pulmonary artery. The tip 103 generally is held in that artery for pressure measurements.

The balloon 104, as better seen in FIG. 3, is formed as a short length of latex tubing, positioned over a necked-down end section 131 of the catheter 101. The distal end of the balloon tubing 104 is doubled under and is held by adhesive to the neck portion 103 of the tip 102.

The proximal end of the balloon tubing 104 is held by adhesive 135 to the proximal end of the necked-down end section 131, and the tapered annular space just proximal to the balloon is filled with epoxy or like cement. A very small balloon-inflation aperture B' is defined in the necked-down end section 131 of the catheter 101, communicating with the dedicated balloon lumen B (FIG. 2).

Three or four centimeters proximal to the tip 102 an aperture T/F' (FIG. 1) is formed in the catheter wall, communicating with the lumen T/F (FIG. 2). This aperture is occupied principally by a thermistor bead T' (FIG. 3), functionally connected at the distal end of the thermistor leads T (FIG. 2). The remainder of the aperture T/F' is filled with urethane or like potting compound 137.

(In FIG. 3 as well as FIG. 1, the catheter 101 and its complementary individual tubes 106 are drawn broken away in their uniform, undistinguished portions 108, to permit illustration of the diameter at a practical scale.)

In use, the balloon 104 and thermistor T' are generally passed with the tip 103 into the patient's pulmonary artery. Temperature information developed with our system thus relates to the blood in that artery.

As indicated roughly in the drawing, the thermistor leads T share the lumen T/F with the optic fibers F. To minimize assembly cost the thermistor leads T and optic fibers F should be drawn together through the thermistor-and-fiber lumen T/F. Doing so may have another advantage—namely, minimizing the risk of damage to both the leads T and the fibers F. This risk, however, we regard as somewhat theoretical since we do not positively know that drawing the leads T and the fibers F sequentially results in damage.

Eighteen to twenty centimeters proximal to the tip 102, another aperture P/M' is formed in the wall of the catheter 101, this one in communication with the lumen P/M. This lumen P/M and aperture P/M' can be left unobstructed, for measurement of pressure in the right ventricle through a fluid column in the lumen; or when desired can be used for heart pacing, as described below.

Within the lumen P/M and extending outward from the catheter 101 through the aperture P/M' is a coaxial wire 139. In use, this wire is typically positioned within the patient's right ventricle, and lies against the myocardium or heart muscle.

Near the tip of the portion of the wire that extends out through the aperture P/M', the central conductor of this wire 139 is exposed so that the outer and inner conductors form an electrode pair for application of pacing voltage pulses to the myocardium. Unused clearance space within the lumen P/M and its aperture P/M' can be used for drip administration of medication—including, for example, dilute heparin solution or other anticoagulant to help maintain the optic fiber distal tip F' (FIG. 4) free of blood clots.

Just distal from the pacing-and-medication aperture P/M', a very short length of stainless-steel spring wire (not shown) is inserted into the lumen P/M. This wire serves to plug the unused, distal portion of this lumen, and also to form a radiopaque marker that can be helpful in positioning the catheter with the aperture P/M' in the patient's right ventricle for proper pacing.

Twenty-eight to thirty centimeters proximal to the tip 102 of the catheter 101, another aperture P' is formed in the catheter wall, communicating with the lumen P. In use this proximal aperture P' is typically positioned within the patient's right atrium, and is used for injection of a cold bolus in the thermodilution method of cardiac output (flow rate) measurement. This same aperture P' can also be used to measure pressures.

Just distal from the proximal aperture P' a very short rod of solid polyvinyl chloride or the like is inserted into the corresponding lumen P, to block off the unused, distal portion of this lumen.

To aid in determining how much of the catheter's length has been inserted into the patient's body during the initial phases of the catheterization process, markers are advantageously imprinted along the outside of the catheter at suitable intervals. For example, indicium 121 may be placed at ten centimeters from the tip 102, indicium 122 at twenty centimeters, and indicium 123 at thirty centimeters.

Each of these indicia may be a simple narrow band or group of narrow bands, each band representing a cumulative ten centimeters. More than four bands being hard to count quickly, however, it is advantageous to use a single broader band for the fifty-centimeter indicium, and then a broad band next to a narrow band to represent fifty plus ten or sixty centimeters, etc. Thus the one-hundred centimeter indicium 124 appears as a pair of broad bands.

The individual termination devices 107 at the proximal end of the catheter include a stopcock 111 that communicates with the balloon lumen B, and a first hub or extension port 112 that communicates with the distal-aperture lumen D. The stopcock 111 is thus for use in inflating (or deflating) the balloon 104. The port 112 is for use in measuring pulmonary-artery pressures or injecting medication into that artery—or, on a drip basis, both simultaneously.

The termination devices also include a fiber-optic connector 113, connected with the optic fibers F in the thermistor/fiber lumen T/F. The polished proximal ends 144 of the fibers F are presented at the proximal side of the connector cap 143 for connection to a mating device (not illustrated) that provides the necessary light sources, detection and interpretation.

In addition, the termination devices 107 include an electrical connector 114, which provides connection points for the thermistor leads T. A threaded section 146 is advantageously provided at the proximal side of the connector cap 145 to securely engage a mating connector of an electronics module that provides excitation and interpretation for the thermistor T'.

Also among the termination devices 107 are two other hubs 115 and 116. Of these, one port 115 communicates with the proximal lumen P, for injection of a cold bolus in thermodilution cardiac-capacity tests. The other port 116 connects with the pacing-and-medication lumen P/M to guide the coaxial pacing wire 139 (and drip medication) to the right ventricle. A Touy-Borst connector allows both electrical hookup to the wire and injection of medicine. (As preferred, a fluid column in the lumen P/M can be used for right-ventricle pressure measurement at the port 116.)

The stopcock 111 and the hub or extension ports 112, 115 and 116 all end in respective liquid-transfer fittings 141, 142, 147 and 148—which are adapted for pressurized attachment of hypodermic-style injecting apparatus.

Conventional sealant, potting, cementing and securing compounds generally available on the open market and familiar to cardiovascular-catheter artisans are used throughout our invention—including the points at which the various parts (e. g., the manifold 105, catheter 101, and single-lumen tubes 106) are held together. As is well known in this field, all components and materials that are to be exposed to the patient's cardiovascular system must be appropriately inert, amenable to sterilization, and preferably supplied sterilized.

It will be understood that the foregoing disclosure is intended to be merely exemplary, and not to limit the scope of the invention—which is to be determined by reference to the appended claims.

We claim:

1. A cardiovascular diagnostic and therapeutic catheter system for determining cardiac output, blood oxygen saturation, and oxygen consumption in a human patient; said system incorporating a catheter of advantageously limited diameter without any interlumen crossovers, and comprising:
   a catheter having at least two lumens and having a distal end adapted for insertion through such patient's vascular system and heart, and having a proximal end adapted for functional attachment to apparatus outside such patient's body;
   a first orifice defined in the side of the catheter at a first measured distance from the distal end, communicating with a first one of the two lumens, and adapted for passage of liquid from the first one of the two lumens into such patient's vascular system;
   injecting means, outside such patient's body and communicating with a proximal portion of the first one of the two lumens, for forcing passage of liquid from the first one of the two lumens through the orifice into such patient's vascular system;

at least one temperature-measuring device disposed along the catheter near its distal end for exposure to temperatures of such patient's vascular system;

long, thin, signal-carrying means, disposed within only the second one of the two lumens, free of interlumen crossover into the first one of the two lumens, and functionally interconnected with the temperature-measuring device;

signal-utilization means, outside such patient's body and interconnected with the signal-carrying means at a proximal portion of the second one of the two lumens, for utilizing said temperature-measuring device to measure the temperature within such patient's vascular system;

whereby the temperature-measuring device and the signal-utilization means in combination are responsive to temperature variations resulting from forced passage of liquid through said first one of the two lumens;

optical-fiber means also disposed within the second one of the two lumens, adapted to project light from the distal end of the catheter into such patient's vascular system and to receive light reflected back from such patient's vascular system, for measurement of oxygen saturation of such patient's blood;

light-emitting means, disposed outside such patient's body and interconnected with the optical-fiber means at a proximal portion of the catheter, for transmitting light through the optical-fiber means to be projected into such patient's vascular system; and light-detecting means, disposed outside such patient's body and interconnected with the optical-fiber means at a proximal portion of the catheter, for receiving light through the optical-fiber means after reflection back from such patient's vascular system, and adapted for interpretation of the received light to determine oxygen saturation of such patient's blood;

wherein said catheter system provides measurements of cardiac output and oxygen saturation, and by calculation therefrom also provides measurement of oxygen consumption in such patient, using only said two lumens and without any interlumen crossover of signal-carrying means.

2. The system of claim 1, further comprising:
an additional lumen defined within the catheter;
an inflatable balloon disposed near the distal end of the catheter and communicating with a distal portion of said additional lumen;
balloon-inflating means outside such patient's body and communicating with a proximal portion of the additional lumen;
said signal-carrying means being entirely outside said additional lumen;
wherein said catheter system provides said measurements and also provides balloon functions, using only three lumens and without any interlumen crossover of signal-carrying means; and
wherein operation of said catheter system is free from risk of balloon deflation due to air leaks associated with the temperature-measuring means.

3. The catheter system of claim 2, for use with a voltage supply outside such patient's body, and further comprising:
yet another lumen defined within the catheter;
a second orifice defined in the side of the catheter at a second measured distance from the distal end, communicating with said yet another lumen;
a coaxial electrical wire disposed within the yet another lumen, and having a proximal end adapted for functional attachment to such outside voltage supply, and having a distal end that projects through the second orifice into such patient's vascular system when the catheter is in such patient's vascular system.

4. The catheter system of claim 3, for use with pressure-measuring means disposed outside such patient's body, and further comprising:
still another lumen defined within the catheter;
an orifice defined in the catheter substantially at the distal end, and communicating with said still another lumen;
means, disposed outside such patient's body for establishing a column of liquid within said still another lumen; and
means for functionally interconnecting such pressure-measuring means to said still another lumen to monitor pressure in the liquid column therein;
whereby the catheter system provides said measurements and in addition such pressure-measuring means monitor pressure within such patient's vascular system, substantially at the distal end of the catheter.

5. The catheter system of claim 2, for use with pressure,-measuring means disposed outside such patient's body, and further comprising:
still another lumen defined within the catheter;
an orifice defined in the catheter substantially at the distal end, and communicating with said still another lumen;
means, disposed outside such patient's body for establishing a column of liquid within said still another lumen; and
means for functionally interconnecting such pressure-measuring means to said still another lumen to monitor pressure in the liquid column therein;
whereby the catheter system provides said measurements and in addition such pressure-measuring means monitor pressure within such patient's vascular system, substantially at the distal end of the catheter.

6. The catheter system of claim 1, for use with a voltage supply outside such patient's body, and further comprising:
yet another lumen defined within the catheter;
a second orifice defined in the side of the catheter at a second measured distance from the distal end, communicating with said yet another lumen;
a coaxial electrical wire disposed within the yet another lumen, and having a proximal end adapted for functional attachment to such outside voltage supply, and having a distal end that projects through the second orifice into such patient's vascular system when the catheter is in such patient's vascular system.

7. The catheter system of claim 6, for use with pressure-measuring means disposed outside such patient's body, and further comprising:
still another lumen defined within the catheter;
an orifice defined in the catheter substantially at the distal end, and communicating with said still another lumen;

means, disposed outside such patient's body for establishing a column of liquid within said still another lumen; and means for functionally interconnecting such pressure-measuring means to said still another lumen to monitor pressure in the liquid column therein;

whereby the catheter system provides said measurements and in addition such pressure-measuring means monitor pressure within such patient's vascular system, substantially at the distal end of the catheter.

8. The catheter system of claim 1, for use with pressure-measuring means disposed outside such patient's body, and further comprising:

still another lumen defined within the catheter;

an orifice defined in the catheter substantially at the distal end, and communicating with said still another lumen;

means, disposed outside such patient's body for establishing a column of liquid within said still another lumen; and means for functionally interconnecting such pressure-measuring means to said still another lumen to monitor pressure in the liquid column therein;

whereby the catheter system provides said measurements and in addition such pressure-measuring means monitor pressure within such patient's vascular system, substantially at the distal end of the catheter.

9. A multipurpose cardiovascular diagnostic and therapeutic catheter system for use with a human patient, and for use with pressure-measuring means disposed outside such patient's body and a voltage supply disposed outside such patient's body, comprising:

a catheter defining exactly five lumens and having a distal end adapted for insertion through such patient's vascular system and heart, and having a proximal end adapted for functional attachment to apparatus outside such patient's body;

an inflatable balloon disposed near the distal end of the catheter and communicating with a distal portion of a first one of the five lumens;

balloon-inflating means outside such patient's body and communicating with a proximal portion of the first one of the five lumens;

a first orifice defined in the side of the catheter at a first measured distance from the distal end, communicating with a second one of the five lumens, and adapted for passage of liquid from the second one of the five lumens into such patient's vascular system;

injecting means, outside such patient's body and communicating with a proximal portion of the second one of the five lumens, for forcing passage of liquid from the second one of the five lumens through the orifice into such patient's vascular system;

a second orifice defined in the side of the catheter at a second measured distance from the distal end, communicating with a third one of the five lumens;

a coaxial electrical wire disposed within the third one of the five lumens, and having a proximal end adapted for functional attachment to such outside voltage supply, and having a distal end that projects through the second orifice into such patient's vascular system when the catheter is in such patient's vascular system;

an orifice defined in the catheter substantially at the distal end, and communicating with the fourth one of the five lumens;

means, disposed outside such patient's body, for establishing a column of liquid within the fourth one of the five lumens;

means for functionally connecting such outside pressure-measuring means to the fourth one of the five lumens to monitor pressure in the liquid column therein;

whereby such pressure-measuring means monitor pressure within such patient's vascular system, substantially at the distal end of the catheter;

at least one electrothermal temperature-measuring device disposed along the catheter near its distal end for exposure to temperatures of such patient's vascular system, and at least two electrical wires disposed within the fifth one of the five lumens and functionally interconnected with the temperature-measuring device;

electrical means, outside such patient's body and interconnected with the two electrical wires at a proximal portion of the fifth one of the five lumens, for utilizing said electrothermal device to measure the temperature within such patient's vascular system;

whereby the electrothermal device and the electrical means in combination are responsive to temperature variations resulting from forced passage of liquid through said second or third one of the five lumens;

optical-fiber means also disposed within the fifth one of the five lumens, adapted to project light from the distal end of the catheter into such patient's vascular system and to receive light reflected back from such patient's vascular system, for measurement of oxygen saturation of such patient's blood;

light-emitting means, disposed outside such patient's body and interconnected with the optical-fiber means at a proximal portion of the catheter, for transmitting light through the optical-fiber means to be projected into such patient's vascular system; and light-detecting means, disposed outside such patient's body and interconnected with the optical-fiber means at a proximal portion of the catheter, for receiving light through the optical-fiber means after reflection back from such patient's vascular system, and adapted for interpretation of the received light to determine oxyge saturation of such patient's blood.

10. The system of claim 9, wherein:
the optical-fiber means comprise at least two optical fibers for transmitting and receiving light in at least two wavelength bands, for determining oxygen saturation of such patient's blood.

11. The system of claim 9, wherein:
the optical-fiber means comprise at least three optical fibers for transmitting and receiving light in at least two wavelength bands, for determining both hematocrit and oxygen saturation of such patient's blood.

12. The system of claim 9, further comprising:
a strength member, also disposed within the fifth one of the five lumens, for protecting the catheter, the optical-fiber means, and the electrical wires against damage due to application of excessive stress to the catheter.

13. The system of claim 9, wherein:
the electrothermal device is a thermistor.

* * * * *